United States Patent [19]
Nomura et al.

[11] Patent Number: 5,645,543
[45] Date of Patent: *Jul. 8, 1997

[54] DISPOSABLE GARMENTS

[75] Inventors: Hironori Nomura; Hirofumi Ohnishi, both of Ehime-ken; Yoshinori Matsura, Kanonji; Tohru Sasaki, Kawanoe, all of Japan

[73] Assignee: Uni-Charm Corporation, Ehime-ken, Japan

[*] Notice: The term of this patent shall not extend beyond the expiration date of Pat. No. 5,334,152.

[21] Appl. No.: 567,834

[22] Filed: Dec. 6, 1995

Related U.S. Application Data

[63] Continuation of Ser. No. 274,440, Jul. 13, 1994, abandoned, which is a continuation of Ser. No. 2,028, Jan. 8, 1993, Pat. No. 5,334,152, which is a continuation of Ser. No. 738,447, Jul. 31, 1991, Pat. No. 5,197,960, which is a continuation of Ser. No. 626,783, Dec. 13, 1990, Pat. No. 5,055,103.

[30] Foreign Application Priority Data

Dec. 18, 1989 [JP] Japan .................... 1-328022

[51] Int. Cl.⁶ .................... A41B 9/00; A61F 13/15
[52] U.S. Cl. .................... 604/385.2; 604/396; 2/401
[58] Field of Search .................... 604/385.2, 366, 604/365.1, 396, 393, 394; 156/161, 164, 229, 496; 2/78 C, 221, 401

[56] References Cited

U.S. PATENT DOCUMENTS

| | | |
|---|---|---|
| 4,300,562 | 11/1981 | Pieniak . |
| 4,323,070 | 4/1982 | Ternstrom . |
| 4,430,086 | 2/1984 | Repke . |
| 4,586,199 | 5/1986 | Birring . |
| 4,606,964 | 8/1986 | Wideman . |
| 4,661,102 | 4/1987 | Shikata . |
| 4,692,163 | 9/1987 | Widlund . |
| 4,726,807 | 2/1988 | Young . |
| 4,743,241 | 5/1988 | Igaue . |
| 4,808,177 | 2/1989 | Des Marais . |
| 4,846,825 | 7/1989 | Enloe . |
| 4,897,084 | 1/1990 | Ternstrom et al. . |
| 5,055,103 | 10/1991 | Nomura . |
| 5,092,861 | 3/1992 | Nomura . |
| 5,147,487 | 9/1992 | Nomura . |
| 5,163,932 | 11/1992 | Nomura . |
| 5,171,239 | 12/1992 | Igaue . |
| 5,188,627 | 2/1993 | Igaue . |
| 5,197,960 | 3/1993 | Nomura . |
| 5,334,152 | 8/1994 | Nomura et al. .......... 604/385.2 |

FOREIGN PATENT DOCUMENTS

| | | |
|---|---|---|
| A-0048011 | 3/1982 | European Pat. Off. . |
| A-0182942 | 6/1986 | European Pat. Off. . |
| A-0405575 | 1/1991 | European Pat. Off. . |
| A-8602530 | 5/1986 | WIPO . |

*Primary Examiner*—John G. Weiss
*Assistant Examiner*—Karin M. Reichle
*Attorney, Agent, or Firm*—Lowe, Price, LeBlanc & Becker

[57] ABSTRACT

Diapers, incontinence pants or baby training pants with two leg openings that each have an upper end portion, a lower end portion, a mid-portion, a crotch portion between the mid-portions, a plurality of elastic members surrounding each leg opening, the plurality of elastic members also extending across the crotch portion in spaced apart lines that are substantially parallel to each other over a substantial portion of the crotch area.

10 Claims, 2 Drawing Sheets

DISPOSABLE GARMENTS

This application is a continuation of application Ser. No. 08/274,440, filed Jul. 13, 1994 and now abandoned, which is a continuation of application Ser. No. 08/002,028, filed Jan. 8, 1993, now U.S. Pat. No. 5,334,152, which is a continuation of application Ser. No. 07/738,447, filed Jul. 31, 1991, now U.S. Pat. No. 5,197,960, which is a continuation of application Ser. No. 07/626,783, filed Dec. 13, 1990, now U.S. Pat. No. 5,055,103, and the benefits of 35 USC 120 are claimed relative to these prior applications.

BACKGROUND OF THE INVENTION

The present invention relates to disposable garments and more particularly to garments such as diapers, incontinence pants and baby training pants.

The garments of such type are usually provided around the respective leg-openings with elastic means. In general, the elastic means are bonded, under stretching, to at least one of the topsheet and the backsheet with adhesive.

With particular garments, for example, a disposable diaper, undesirable leakage of excretions often occurs, regardless of the user's gender, at the opposite side of the crotch area defined between the opposite leg-openings due to location and orientation of the urinary organs.

Accordingly, it is preferred to provide an arrangement such that the elastic means have a higher tensile stress at the mid-portion of each leg-opening than at the remaining area and thereby allow the diaper to contact with the wearer's skin at this area with a higher fitness.

In view of the fact that, after put on the user, the diaper can move relative to the wearer's skin at the upper end portion and lower end portion of each leg-opening more easily than at said, mid-portion it is preferred also to decentralize the tensile stress of the elastic means at said upper end portion and lower end portion, allowing the diaper to contact with the wearer's skin over a relatively large area with a moderate fitness.

However, in the diapers that have been proposed and commonly used in practice, no consideration can be found about gradually varying the tensile stress of the elastic means around the leg-openings and decentralizing the said tensile stress depending upon the location around the leg-openings.

It is a first object of the invention to provide the disposable garments including elastic means surrounding each leg-opening which has a tensile stress gradually decreasing from adjacent the mid-portion toward the upper end portion and lower end portion of the leg-opening.

It is a second object of the invention to provide disposable garments including elastic means surrounding each leg-opening with a tensile stress gradually decentralized from adjacent the mid-portion toward the upper end portion and lower end portion of the leg-opening.

SUMMARY OF THE INVENTION

The first object set forth above is achieved, in accordance with the invention, by disposable garments having a topsheet, a backsheet and elastic means provided around leg-openings defined at opposite sides of a crotch area connecting front and rear sections of the top- and backsheets, wherein the elastic means surrounding each of the leg-openings comprises first and second elastic members, the first elastic member is positioned substantially along a front half of the leg-opening while the second elastic member is positioned substantially along a rear half of the leg-opening so that the first and second elastic members intersect each other at their longitudinally inner ends located adjacent the mid-portion of the leg-opening, and the first and second elastic members have their tensile stress gradually decreasing from the longitudinally inner ends toward their longitudinally outer ends.

The second object set forth above is achieved, according to the invention, by disposable garments as has been described above, wherein the elastic means surrounding each of the leg-openings comprises a plurality of first elastic members and a plurality of second elastic members and the first and second elastic members have their inter-member spacings gradually enlarged from their longitudinally inner ends toward their longitudinally outer ends.

In a preferred embodiment, the first and second elastic members surrounding each of the leg-openings are continuous to those surrounding the opposite leg-opening, respectively and intermediate lengths of the respective continuous elastic members connecting the opposite leg-openings extend across the crotch area transversely thereof.

In this manner, the invention allows the garments to contact with the wearer's skin adjacent the mid-portion of each leg-opening under a higher fitness than at the upper end portion and lower end portion thereof, since the first and second elastic members have the tensile stress gradually decreasing from their longitudinally inner ends toward their longitudinally outer ends, i.e., gradually increasing from their longitudinally outer ends toward their longitudinally inner ends.

Furthermore the tensile stress of the first and second elastic members is transversely decentralized in the proximity of the upper end portion and lower end portion of each leg-opening, since the first and second elastic members comprise a plurality of members, respectively, and their inter-member spacings are gradually enlarged from their longitudinally inner ends toward their longitudinally outer ends.

By using such garments of the invention, leakage of excretions readily occurring through the mid-portion of each leg-opening, which has conventionally been remarkable and almost inevitable, can be now effectively alleviated, since the invention allows the elastic members to contact with the wearer's skin in the proximity of the mid-portion of each leg-opening under a relatively firm fitness.

In addition, the upper and lower end portions of each leg-opening most readily movable relative to the wearer's skin can be maintained in contact with the wearer's skin under a relatively weak tensile stress but over a large area, since the tensile stress of the elastic members is decentralized in the vicinity of the upper and lower end portions of each leg-opening.

PREFERRED EMBODIMENT OF THE INVENTION

The other features and advantages of the invention will be readily understood from the following description made in reference with the accompanying drawings.

Figures 1, 2:
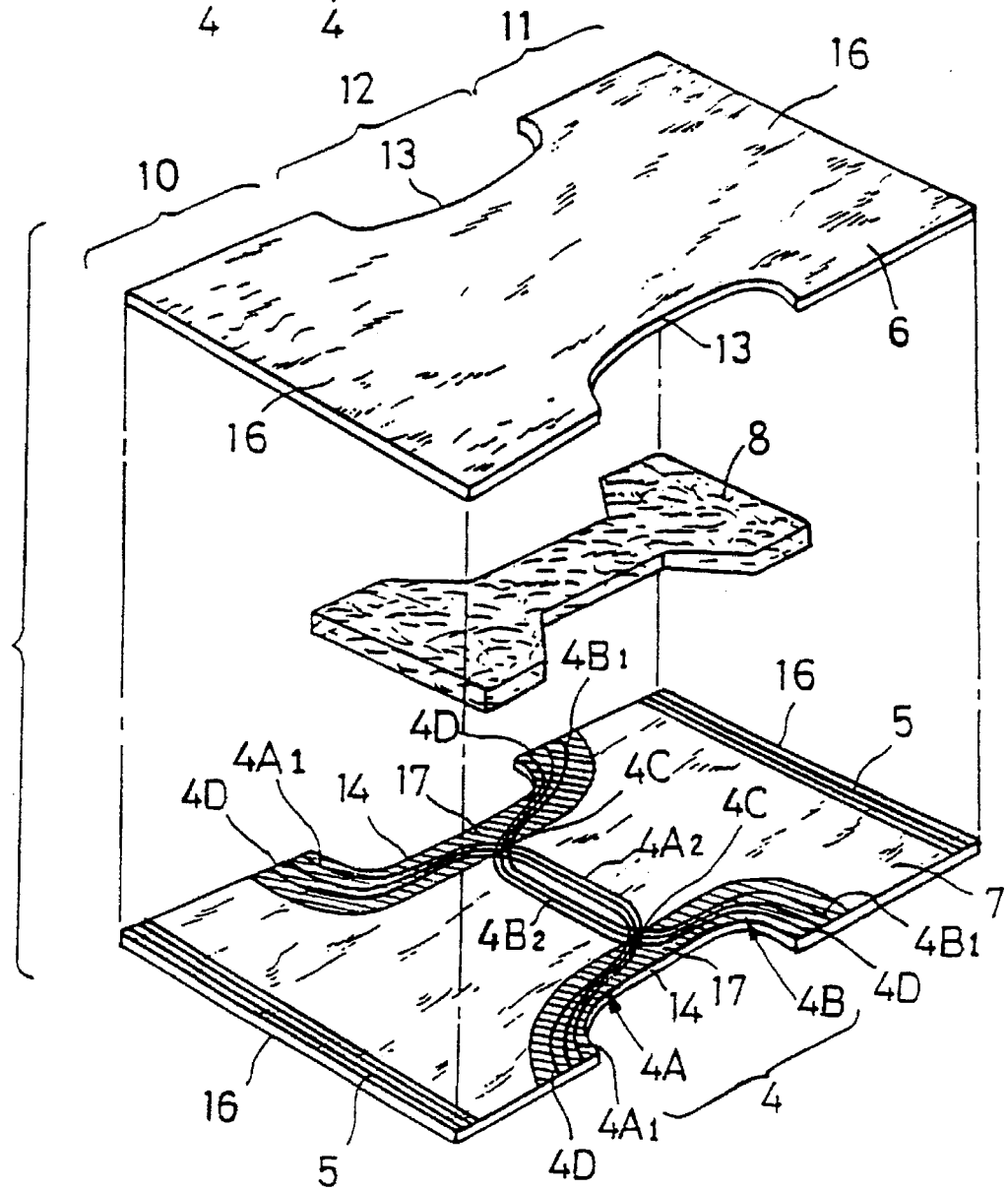
FIG. 1 is a perspective view showing an embodiment of an assembled garment constructed in accordance with the teaching of the invention.
FIG. 2 is an exploded unassembled perspective view of the garments.

Referring first to FIG. 1, a diaper of pants type 1 is shown in a perspective view. As shown, the diaper 1 has leg-openings 2 and a waist-opening 3, both being provided with elastic means 4, 5, respectively.

Referring to FIG. 2, the same diaper 1 is shown in an exploded unassembled perspective view. As illustrated, the diaper 1 comprises a water-permeable topsheet 6 being stretchable both in length and width, a water-permeable backsheet 7 being also stretchable both in length and width, a mat- or sheet-like water-absorbent core 8, and the elastic means 4, 5 surrounding the leg-openings 2 and the waist-opening 3, respectively. Front and rear sections 10, 11 of the top and backsheets 6, 7 define between the front and rear sections 10, 11 a crotch area 12 having opposite side edges formed with identical notched edges 13, 14, respectively, so as to define the respective leg-openings 2. The backsheet 7 may include water-impermeable plastic film (not shown) being stretchable both in length and width and bonded to the inner side of the backsheet 7 with adhesive intermittently applied thereto. Such arrangement will perfectly prevent excretions from passing through the backsheet 7. Where the film is bonded at least along its outer peripheral area to the topsheet 6 with intermittently placed spots of adhesive, the top- and backsheets 6, 7 as components of the diaper 1 will be improved not only in elasticity but also in tensile stress and thereby the fitness characteristic of the diaper 1 on the wearer's body will be further improved.

The elastic means 4 associated with the leg-openings comprises a plurality of first elastic members 4A and a plurality of second elastic members 4B. The first and second elastic members 4A, 4B extend in parallel to each other along their intermediate lengths $4A_2$, $4B_2$ and intersect each other substantially at middle points along the respective notched edges 13, 14, then extensions $4A_1$, $4B_1$ diverge from the respective intersections 4C so as to extend along the respective notched edges 13, 14. The divergent extensions $4A_1$, $4B_1$ are bonded to the inner surface(s) of the back- and/or topsheet(s) with adhesive 17 but the intermediate parallel lengths $4A_2$, $4B_2$ are positioned in substantially in a central area of the core across the crotch area 12 without being bonded to any of the back- and topsheets.

The first and second elastic members 4A, 4B are so arranged that the respective divergent extensions $4A_1$, $4B_1$ have the tensile stress gradually decreasing from their longitudinally inner ends (said respective intersections) 4C corresponding to the mid-portions of the respective leg-openings toward their longitudinally outer ends 4D corresponding to the upper and lower end portions of the respective leg-openings, i.e., gradually increasing from their longitudinally outer ends 4D toward their longitudinally inner ends 4C.

In addition, a plurality of the first elastic members 4A and a plurality of the second elastic members 4B are so arranged to have their inter-member spacings along the respective divergent extensions $4A_1$, $4B_1$ gradually enlarged from their longitudinally inner ends 4C (said respective intersections) toward their longitudinally outer ends 4D, i.e., gradually reduced from their longitudinally outer ends 4D toward their longitudinally inner ends 4C (said respective intersections) and their inter-member spacings initially decreased as the elastic members approach respective side portions of respective leg-openings from the crotch area.

Figure 3:
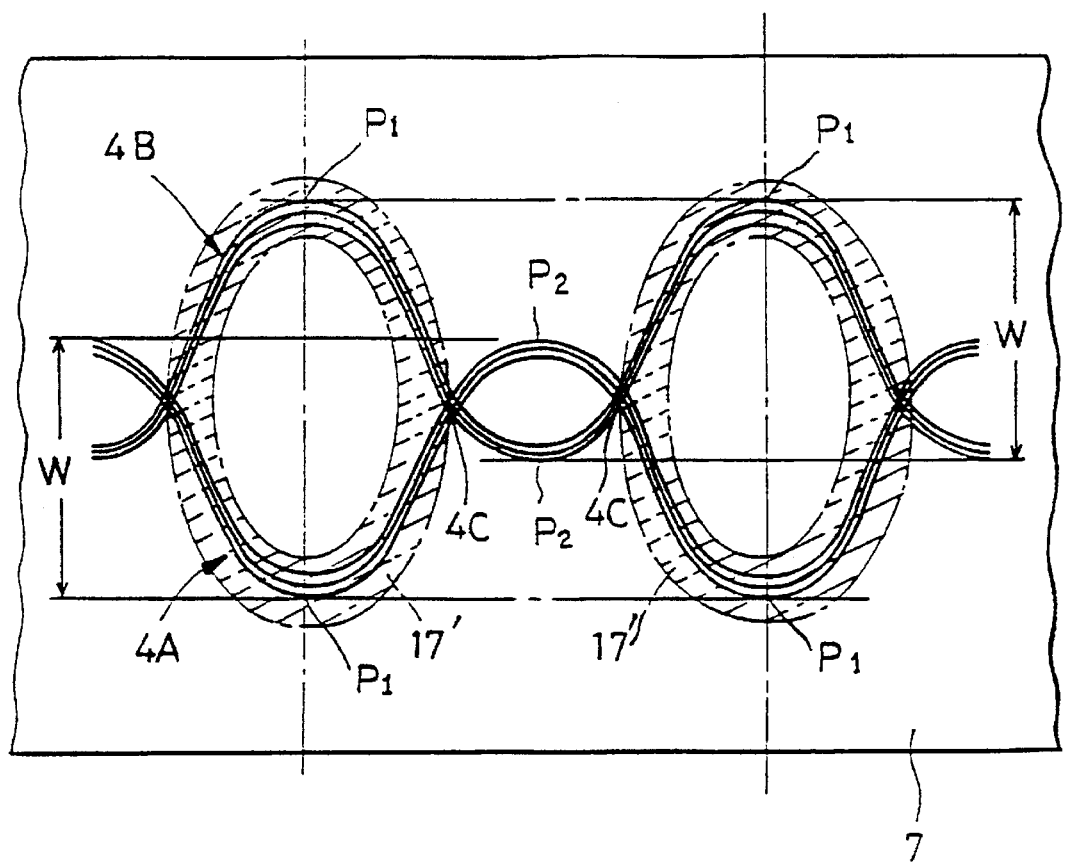
FIG. 3 is a plan view showing by way of example the manner in which elastic the means is arranged in an unassembled garment.

FIG. 3 is a plan view illustrating by way of example the manner in which the first and second elastic members 4A, 4B are arranged as has been described above. Adhesive is applied onto the backsheet 7 at given intervals longitudinally thereof so as to surround successive ellipses and thereby to define adhesive areas 17' while the backsheet 7 is moved longitudinally thereof at a given velocity. Simultaneously, a plurality of the first continuous elastic members 4A and a plurality of the second continuous elastic members 4B, both being stretched at a given elongation percentage, are inserted into the corresponding number of first and second traverses (not shown) which are, in turn, activated so that the first and second elastic members 4A, 4B are bonded to the backsheet 7 along the adhesive areas 17', describing curves substantially corresponding to sine curves. These curves are symmetric with respect to a longitudinally center line of the backsheet 7. The first and second elastic members 4A, 4B travel from a starting point $P_1$ to a turning point $P_2$, then from the turning point $P_2$ to the new starting point $P_1$, respectively, by a width W for each cycle. Their elongation percentage increases during travel from the starting point $P_1$ to the turning point $P_2$ and consequently their tensile stress also increases, since the first and second elastic members 4A, 4B under stretching with a given elongation percentage having been linearly traveling longitudinally of the backsheet 7 are forcibly deflected by said traverses transversely of the backsheet 7, resisting against such deflection, and, as a consequence, the first and second elastic members 4A, 4B are stretched in the course of traveling from the starting point $P_1$ to the turning point $P_2$, respectively. It will be understood that said elongation percentage depends upon the velocity at which the first and second elastic members 4A, 4B are fed longitudinally of the backsheet 7 as well as the velocity at which said traverses move transversely of the backsheet 7. Meanwhile, spacings of component elastic members in each plurality of elastic members 4A, 4B are reduced as each plurality of elastic members 4A, 4B having been linearly traveling longitudinally of the backsheet 7 is forcibly deflected by the associated traverse transversely of the backsheet 7 from the starting point $P_1$ to the turning point $P_2$. It will be understood here again that a degree of such inter-member spacing reduction depends upon the velocity at which the first and second elastic members 4A, 4B as well as the backsheet 7 travel.

The lengths (the intermediate parallel length $4A_2$, $4B_2$ in FIG. 2) of the first and second elastic members 4A, 4B extending between each pair of intersections 4C and being closely adjacent to each other are loosened to be brought further close together since the area of the backsheet 7 corresponding to these intermediate parallel lengths $4A_2$, $4B_2$ carries no adhesive. However, these intermediate parallel lengths also may be bonded to the backsheet 7 with adhesive, if desired, by applying adhesive onto said area of the backsheet 7 or the first and second elastic members 4A, 4B may be entirely coated with adhesive. In the latter case, obviously no adhesive will be applied onto the backsheet 7 at all.

The elastic means 5 surrounding the waist-opening is bonded to inner surface(s) of the top- and/or backsheet(s) with adhesive along a waist line 16.

Though not shown, the core 8 is bonded, on its top side and/or bottom side, to the topsheet 6 and/or the backsheet 7 with spots of adhesive intermittently placed thereon. A laminar structure formed in this manner may be folded in two along its longitudinally center line and then opposite free edges thereof may be joined together by means of heat seal to provide the individual diaper 1 as shown by FIG. 1.

Such diaper 1 may be obtained by employing the method for making disposable briefs as disclosed in Japanese Pat. Application No. 1989-167224 filed in the name of the same applicant as of the present application. However, it should be understood that the present invention is not limited to the form of pants or briefs. Specifically, it is possible within the scope of the invention that, instead of folding said laminar structure along its longitudinally center line in two followed by joining the opposite free edges together by means of heat seal, the rear section 11 of said laminar structure is provided at opposite sides with suitable fastener means such as strips of pressure tape by which the waist line 16 of the laminar structure (garments) is fixedly completed as in the case of so-called open type diaper. It is also possible even to omit the core 8, depending upon the type of garments.

The topsheet 6 and the backsheet 7 may be of water-permeable nonwoven fabric being stretchable both in length and width, the core 8 may be of fluffy pulp mixed with highly water-absorbent polymer particles, and the elastic members may be of natural or synthetic rubber or the like.

What is claimed is:

1. A disposable garment in assembled condition comprising:
   a topsheet and a backsheet disposed in an overlying relationship,
   spaced apart first and second leg openings, each leg opening having an upper end portion, a lower end portion, a mid-portion between said upper end portion and said lower end portion, a front side portion generally disposed between said upper end portion and said mid-portion, and a rear side portion generally disposed between said mid-portion and said lower end portion,
   a crotch area extending between said mid-portions of said leg openings,
   means for elastically surrounding each of said leg openings, the improvement comprising
      said means for elastically surrounding each of said leg openings comprising a plurality of first elastic members and a plurality of second elastic members,
      said first elastic members extending along the front side portion of said first leg opening, across said crotch area and then along one of said side portions of said second leg opening,
      said second elastic members extending along the rear side portion of said first leg opening, across said crotch area and then along the other of said side portions of said second leg opening,
      said plurality of first and second elastic members converging toward each other from said lower end portion toward said mid-portion of each leg opening and extending across said crotch area along lines that are generally parallel to each other over a substantial portion of the crotch area,
      the tensile stress of said plurality of first and second elastic members decreasing toward the upper end portion of each leg opening.

2. A disposable garment in assembled condition comprising:
   a topsheet and a backsheet disposed in an overlying relationship,
   spaced apart first and second leg openings, each leg opening having an upper end portion, a lower end portion, a mid-portion between said upper end portion and the lower end portion, a front side portion generally disposed between said upper end portion and said mid-portion, and a rear side portion generally disposed between said mid-portion and said lower end portion,
   a crotch area extending between said mid-portions of said leg openings,
   means for elastically surrounding each of said leg openings, the improvement comprising
      said means for elastically surrounding each of said leg openings comprising a plurality of first elastic members and a plurality of second elastic members,
      said first elastic members extending along the front side portion of said first leg opening, across said crotch area and then along one of said side portions of said second leg opening,
      said second elastic members extending along the rear side portion of said first leg opening, across said crotch area and then along one of said side portions of said second leg opening,
      the spacing between each of said plurality of first elastic members gradually increasing from said crotch area toward said upper end portion of said first leg opening and the spacing between each of said second elastic members gradually increasing from said crotch area toward said lower end portion of said first leg opening.

3. A disposable garment in assembled condition according to claim 2 wherein the tensile stress of said plurality of first and second elastic members decreases toward the upper end portion of each leg opening.

4. A disposable garment in assembled condition according to claim 2, wherein the spacing between each of said plurality of first elastic members initially decreases as said plurality of first elastic members approach said one of said side portions of said second leg opening from said crotch area.

5. A disposable garment in assembled condition according to claim 4, wherein the spacing between each of said plurality of second elastic members initially as said plurality of second elastic members approach said other of said side portions of said second leg opening from said crotch area.

6. A disposable garment in assembled condition comprising:
   a topsheet and a backsheet disposed in an overlying relationship,
   spaced apart first and second leg openings, each leg opening having an upper end portion, a lower end portion, a mid-portion between said upper end portion and said lower end portion, a front side portion generally disposed between said upper end portion and said mid-portion, and a rear side portion generally disposed between said mid-portion and said lower end portion,
   a crotch area extending between said mid-portions of said leg openings,
   elastic means for surrounding each of said leg openings, the improvement comprising
      said elastic means for surrounding each of said leg openings comprising a plurality of first elastic members and a plurality of second elastic members,
      said first elastic members extending along at least most of the front side portion of said first leg opening, across said crotch area and then along at least a portion of one of said side portions of said second leg opening,
      said second elastic members extending along at least most of the rear side portion of said first leg opening, across said crotch area and then along at least a portion of said other of said side portions of said second leg opening,
      said plurality of first and second elastic members converging toward each other toward said mid-portion of each leg opening,
      the tensile stress of said first and second elastic members varying along the length of the portions of said elastic members adjacent each leg opening.

7. A disposable garment in assembled condition according to claim 6, wherein said plurality of first elastic members and said plurality of second elastic members extend across said crotch area along lines that are generally parallel to each other.

8. A disposable garment in assembled condition comprising:

a topsheet and a backsheet disposed in an overlying relationship, spaced apart first and second leg openings, each leg opening having an upper end portion, a lower end portion, a mid-portion between said upper end portion and said lower end portion, a front side portion generally disposed between said upper end portion and said mid-portion, and a rear side portion generally disposed between said mid-portion and said lower end portion, a crotch area extending between said mid-portions of said leg openings, and means for elastically surrounding each of said leg openings, the improvement comprising said means for elastically surrounding each of said leg openings comprising a plurality of first elastic members and a plurality of second elastic members, said first elastic members extending along the front side portion of said first leg opening and along one of said side portions of said second leg opening, said second elastic members extending along the rear side portion of said first leg opening and along the other of said side portions of said second leg opening, the spacing between said plurality of first elastic members gradually increasing toward said upper end portion of said first leg opening and the spacing between said second elastic members gradually increasing toward said lower end portion of said first leg opening.

9. A disposable garment in assembled condition according to claim 8, wherein the spacing between each of said plurality of first elastic members initially as said plurality of first elastic members approach said one of said side portions of said second leg opening from said crotch area.

10. A disposable garment in assembled condition according to claim 9, wherein the spacing between each of said plurality of second elastic members initially decreases as said plurality of second elastic members approach said other of said side portions of said second leg opening from said crotch area.

* * * * *